(12) United States Patent
Reis

(10) Patent No.: US 7,947,061 B1
(45) Date of Patent: May 24, 2011

(54) RATCHETING TOURNIQUET APPARATUS

(75) Inventor: Ricardo A Reis, Elizabeth, NJ (US)

(73) Assignee: Fast-T, LLC, Pleasantville, NY (US)

( * ) Notice: Subject to any disclaimer, the term of this patent is extended or adjusted under 35 U.S.C. 154(b) by 308 days.

(21) Appl. No.: 11/863,059

(22) Filed: Sep. 27, 2007

(51) Int. Cl.
*A61B 17/00* (2006.01)

(52) U.S. Cl. ....................................... 606/203

(58) Field of Classification Search ................ 606/204, 606/203, 201, 157; 602/16; 2/310, 338; 24/442, 306
See application file for complete search history.

(56) References Cited

U.S. PATENT DOCUMENTS

| 4,640,281 | A | 2/1987 | Sturm et al. |
| 5,314,437 | A | 5/1994 | Holtsch |
| 6,149,618 | A | 11/2000 | Sato |
| 6,402,713 | B1* | 6/2002 | Doyle ............................ 602/26 |
| 6,884,254 | B2 | 4/2005 | Brooks |
| 6,899,720 | B1* | 5/2005 | McMillan ..................... 606/203 |
| 2003/0028215 | A1 | 2/2003 | Brooks |
| 2005/0049630 | A1* | 3/2005 | Ambach ....................... 606/203 |
| 2005/0113866 | A1 | 5/2005 | Heinz et al. |
| 2006/0025807 | A1 | 2/2006 | Licata et al. |
| 2008/0051827 | A1* | 2/2008 | McEwen ....................... 606/202 |

* cited by examiner

*Primary Examiner* — Todd E Manahan
*Assistant Examiner* — Christopher Schubert
(74) *Attorney, Agent, or Firm* — Brian S. Steinberger; Law Offices of Brian S. Steinberger, P.A.

(57) ABSTRACT

A ratcheting tourniquet apparatus having a quick adjustment mechanism for initial tourniquet strap approximation, and a ratcheting assembly for fine, stringent strap adjustment about a limb of a patient. The apparatus provides for quick and easy use, even to the uninitiated. The apparatus provides for sufficient leverage via the ratcheting assembly such that severe tightening of the strap is possible as needed. The apparatus quick adjustment mechanism further provides instant tourniquet release.

2 Claims, 3 Drawing Sheets

RATCHETING TOURNIQUET APPARATUS

BACKGROUND OF THE INVENTION

Tourniquets have long been used for controlling and stopping the flow of blood to an extremity. EMS, police, and military personnel offer prime examples. Tourniquets are used in emergency situations and also can be used in surgeries. In order to be effective a tourniquet must be capable of tightening sufficiently to halt blood flow to the extremity, and to also provide easy adjustment whereby it can be loosened and tightened as needed. Sufficient tightening typically requires a leverage advantage; therefore a means for tightening that supplies such should be provided. Also, a tourniquet must be easily operable by an inexperienced individual, whether the wearer or someone providing treatment to the patient. A tourniquet ideally provides for rapid use, as a life-threatening condition often exists with tourniquet use. A basic design is therefore desirable, and one which provides for immediate understanding of use. Additionally, a tourniquet must be fully operational in inclement weather conditions.

Further, a lightweight inexpensively produced design is desirable, thereby enabling more widespread transport and use of the tourniquet.

FIELD OF THE INVENTION

The ratcheting tourniquet apparatus relates to tourniquets and more especially to a tourniquet which provides both a quick adjustment and a ratcheting fine adjustment.

SUMMARY OF THE INVENTION

The general purpose of the ratcheting tourniquet apparatus, described subsequently in greater detail, is to provide a ratcheting tourniquet apparatus which has many novel features that result in an improved ratcheting tourniquet apparatus which is not anticipated, rendered obvious, suggested, or even implied by prior art, either alone or in combination thereof.

To attain this, the ratcheting tourniquet apparatus is lightweight, easily transported, such as in a coat pocket or the like. The apparatus can also be carried by being looped around a belt or other piece of equipment. The basic design of the apparatus provides for inexpensive production and for easily understood usage, especially in life-threatening situations. The pliable strap can be made of woven natural or synthetic fiber, for example, or even non-woven pliable material.

The ratchet assembly can be metal or synthetic material, such as plastic, as can be the quick adjustment mechanism. The width of the apparatus can be varied, such as ½ inch wide or 2 inches wide. The insertion end of the strap is quickly identifiable by both the rigid non-slip surface and by color, such as red. This offers a guide to the uninitiated user, as well as the experienced user in inclement conditions, for insertion of the strap. The rigid end also provides for easy insertion, as opposed to a pliable end for the strap. Once the strap is looped around the patient's limb and the inserted into the quick adjustment mechanism, the strap is snugly pulled and the cam lock lever pushed to prevent strap slippage. This usage condition provides that the toothed tongue has been initially inserted into the ratchet assembly. In this condition, the ratchet assembly is used to tighten the strap of the apparatus more stringently about the limb, as needed.

Conversely, the strap can be inserted into the quick adjustment mechanism without the toothed tongue inserted into the ratchet assembly. In this condition, the user passes the strap through the quick adjustment mechanism until the strap is approximated a correct length. The toothed tongue is then inserted into the ratchet assembly and the ratchet lever used to tighten the strap further.

With the need to loosen or remove the apparatus from a limb, the quick adjustment mechanism cam lock lever is lifted to allow the strap to slacken. The loss of strap tension allows the lock block of the ratchet assembly to release.

Thus has been broadly outlined the more important features of the improved ratcheting tourniquet apparatus so that the detailed description thereof that follows may be better understood and in order that the present contribution to the art may be better appreciated.

An object of the ratcheting tourniquet apparatus is to be inexpensively produced.

Another object of the ratcheting tourniquet apparatus is to easily used by a professional or amateur.

A further object of the ratcheting tourniquet apparatus is to rapidly usable.

An added object of the ratcheting tourniquet apparatus is to basic.

Yet a further object of the ratcheting tourniquet apparatus is to be lightweight and portable.

And, an object of the ratcheting tourniquet apparatus is to provide a quick course adjustment mechanism.

Yet another object of the ratcheting tourniquet is to provide an additional mechanism for fine adjustment.

Still another object of the ratcheting tourniquet is to provide for mechanical leverage advantage in tightening the fine adjustment.

These together with additional objects, features and advantages of the improved ratcheting tourniquet apparatus will be readily apparent to those of ordinary skill in the art upon reading the following detailed description of presently preferred, but nonetheless illustrative, embodiments of the improved ratcheting tourniquet apparatus when taken in conjunction with the accompanying drawings.

In this respect, before explaining the current embodiments of the improved ratcheting tourniquet apparatus in detail, it is to be understood that the ratcheting tourniquet apparatus is not limited in its application to the details of construction and arrangements of the components set forth in the following description or illustration. Those skilled in the art will appreciate that the concept of this disclosure may be readily utilized as a basis for the design of other structures, methods, and systems for carrying out the several purposes of the improved ratcheting tourniquet apparatus. It is therefore important that the claims be regarded as including such equivalent constructions insofar as they do not depart from the spirit and scope of the ratcheting tourniquet apparatus. It is also to be understood that the phraseology and terminology employed herein are for purposes of description and should not be regarded as limiting.

DETAILED DESCRIPTION OF THE DRAWINGS

With reference now to the drawings, and in particular FIGS. 1 through 5 thereof, the principles and concepts of the ratcheting tourniquet apparatus generally designated by the reference number 10 will be described.

Figure 1:
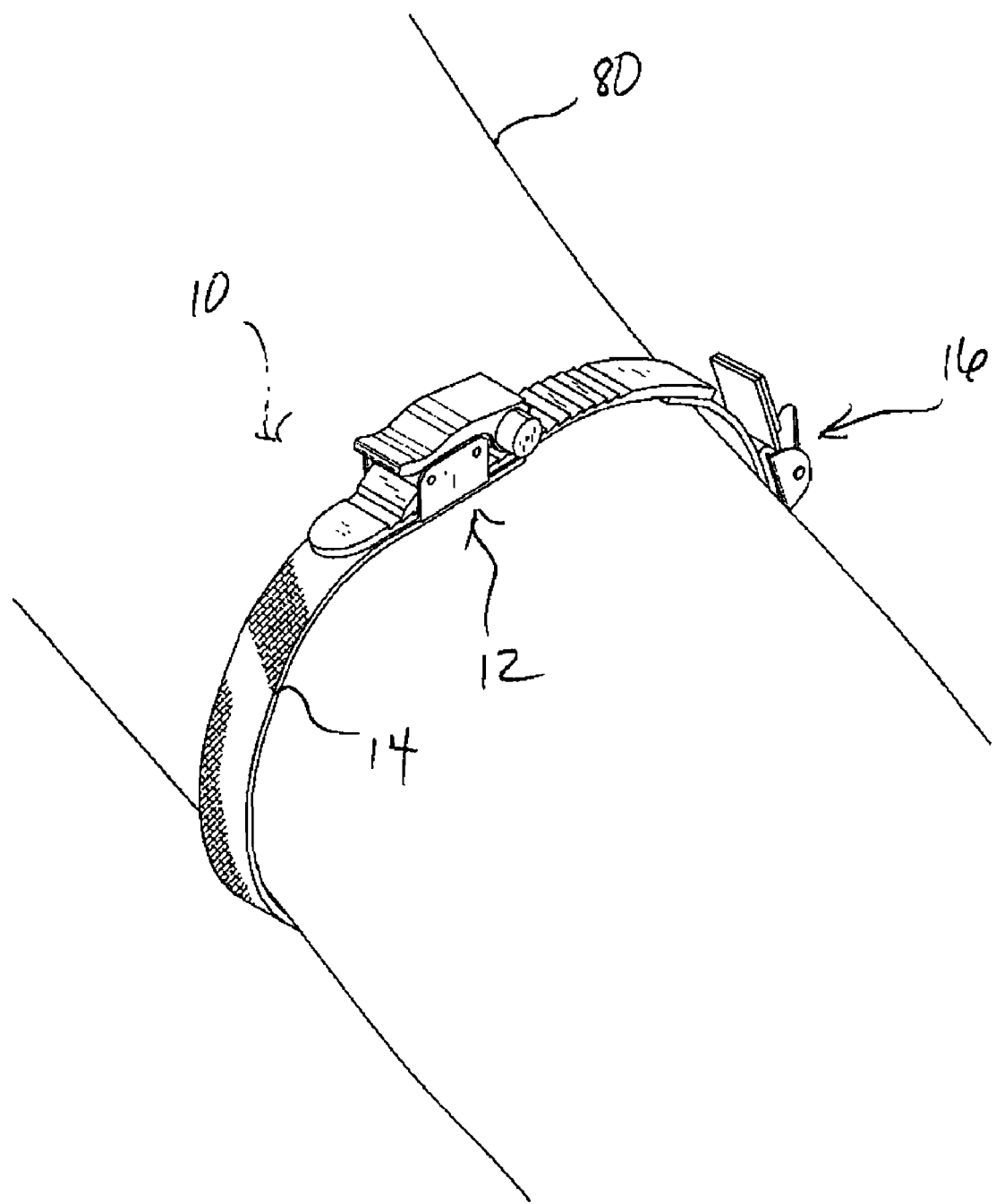
FIG. 1 is a perspective view of the apparatus in use.
Figure 2:
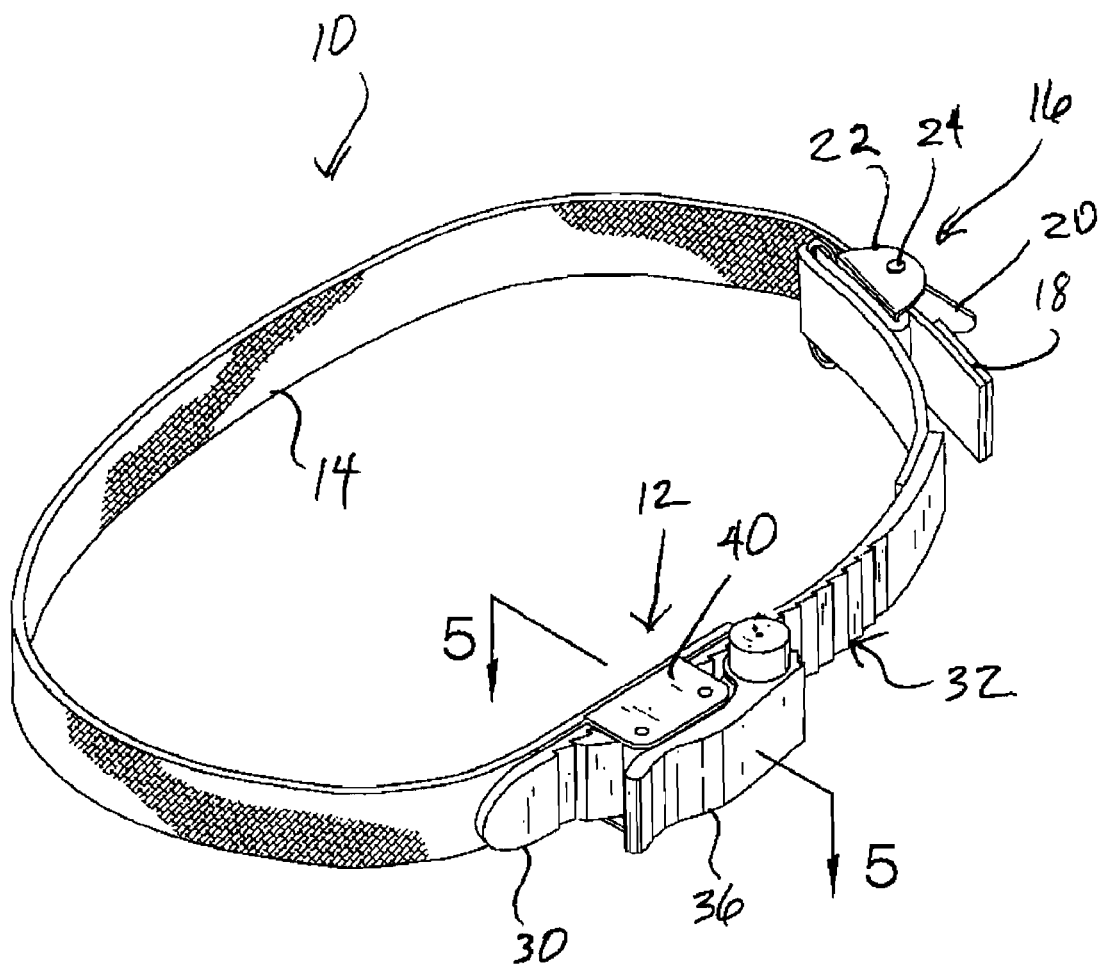
FIG. 2 is a perspective view.
Figure 3:
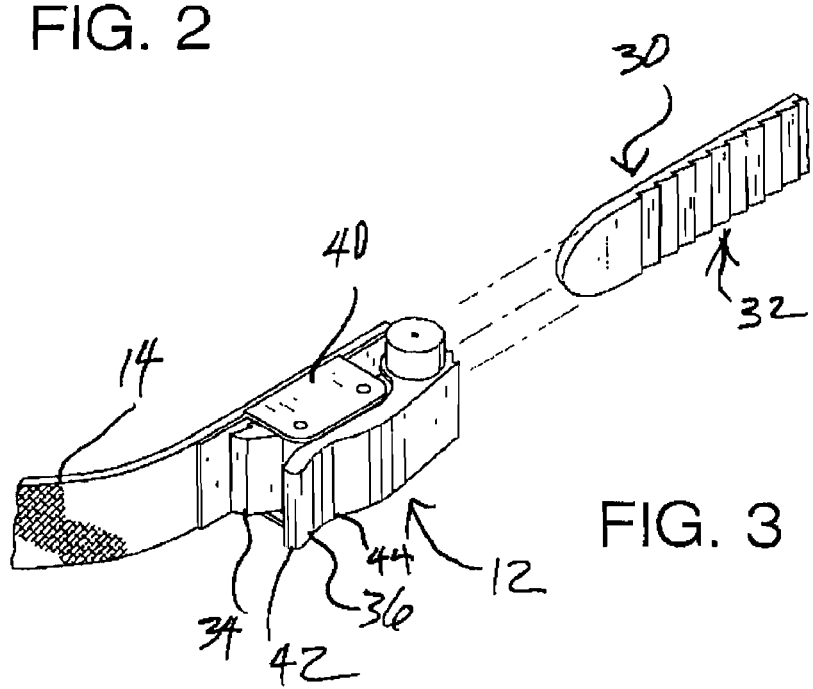
FIG. 3 is perspective view with tongue disengaged from the ratchet assembly.
Figure 4:
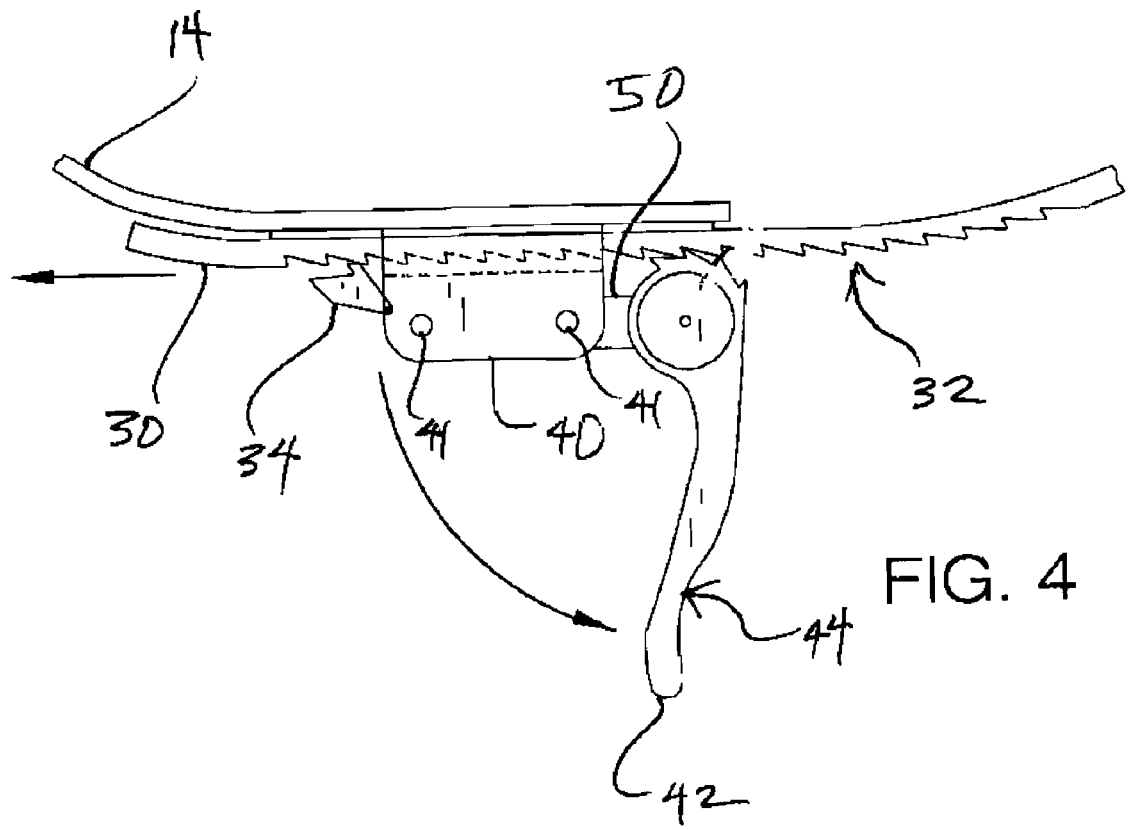
FIG. 4 is a lateral elevation view of the ratchet assembly with tongue inserted and toothed lever in a tightening mode, the lock block in preparation of receiving another tooth of the tongue teeth.
Figure 5:
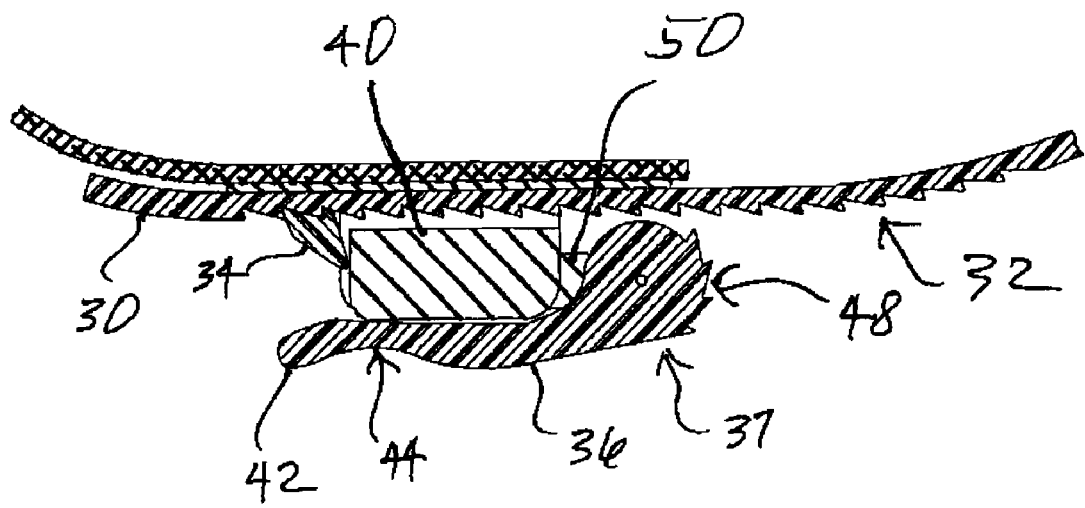
FIG. 5 is a cross sectional view of the ratchet assembly of FIG. 1.

Referring to FIG. 1, the ratcheting tourniquet apparatus 10 illustrates use on a patient's arm/leg/limb 80. The ratchet assembly 12 is engaged, and the quick adjustment mechanism 16 is engaged, thereby securing the apparatus around the limb 80.

Referring to FIGS. 2-5, the apparatus 10 comprises a pliable strap 14 for encircling a limb 80 of a patient. The rigid insertion end 18 of the strap 14 further comprises a gripping surface which is ideally visually identified quickly by means of color, such as red. The rigid easily identifiable insertion end 18 provides a visual and tactile guide for the first step in applying the apparatus 10 to patient. The rigid insertion end 18 provides for positive insertion of the strap 14 into the quick adjustment mechanism 16, even in inclement conditions or darkness. The quick adjustment mechanism 16 comprises a cam lock anchor 22 having two spaced apart sides and a bottom. The cam lock pivot 24 is spaced apart from the bottom sufficiently for the insertion end 18 and the strap 14 to pass through. The cam lock lever 20 is pivotally affixed to the cam lock pivot 24 and is thereby disposed between the cam lock anchor 22 sides. The cam lock lever 20 selectively holds and releases the strap 14. When the cam lock lever 20 is positioned approximately parallel to the strap 14, the strap 14 is engaged and prevented from slip.

The quick adjustment mechanism 16 provides for the tourniquet apparatus 10 to be quickly applied prior to more stringent tightening with the ratchet assembly 12. The quick adjustment mechanism 16 also provides for instant loosening of the apparatus 10. The tongue 30 comprises teeth 32 on one side. The tongue 30 is extended from the quick adjustment mechanism 16. The ratchet assembly 12 is affixed to the end of the strap 14 opposite the insertion end 18. The ratchet assembly 12 comprises the ratchet frame 40 having a bottom and two spaced apart sides, an entry and an exit. The support 50 is secured between the two spaced apart sides of the ratchet frame 40 by the frame connectors 41. The support 50 is spaced apart from the ratchet frame 40 bottom to allow passage of the tongue 30. The ratchet lever 36 is disposed prior to the entry of the ratchet frame 40. The ratchet lever 36 is pivotally secured to the support 50. The ratchet lever 36 further comprises a bulbous end 37 partially comprising lever teeth 48. The lock block 34 is pivotally disposed at the exit of the ratchet frame 40. The lock block 34 prevents the toothed tongue 30 from slipping backward toward disengagement from the ratchet assembly 12 when the ratchet lever 36 is positioned parallel to the tongue 30. Therefore, lifting the ratchet lever 36 causes the lever teeth 48 to engage the teeth 32 of the tongue 30, thereby further tightening the strap 14 around the limb 80 of a patient. The tension of the tightened strap 14 automatically prevents the toothed lock block 34 from disengagement from the tongue 30. The ratchet lever 36 further comprises the depression 44 proximal to the end of the ratchet lever 36 opposite the bulbous end 37.

As significant force is sometimes required to tighten any tourniquet, as well as this tourniquet apparatus 10, the depression 44 provides a means of increased contact area on the ratchet lever 36, for a thumb for example, so that force is more readily applied. The ratchet lever 36 further comprises an elevation 42 at the end of the ratchet lever 36 opposite the bulbous end 37. The elevation 42 provides for a user to more readily and easily initially lift the ratchet lever 36 from the position of lever teeth 48 disengagement to engagement with the teeth 32 of the tongue 30.

With respect to the above description then, it is to be realized that the optimum dimensional relationships for the parts of the ratcheting tourniquet apparatus, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the ratcheting tourniquet apparatus.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the ratcheting tourniquet apparatus may be used.

Therefore, the foregoing is considered as illustrative only of the principles of the ratcheting tourniquet apparatus. Further, since numerous modifications and changes will readily occur to those skilled in the art, it is not desired to limit the ratcheting tourniquet apparatus to the exact construction and operation shown and described, and accordingly, all suitable modifications and equivalents may be resorted to, falling within the scope of the ratcheting tourniquet apparatus.

What is claimed is:

1. A ratcheting tourniquet apparatus, consisting of:
    a single belt strap having a colored rigid insertion end and an opposite end having a single ratcheting assembly having an insertion opening and an exit opening;
    a single elongated tongue having a protruding end with a teethed surface, the tongue extending from a single quick adjustment mechanism that has an insertion opening and an exit opening,
    wherein a single closed loop is formed from the colored rigid insertion end of the single belt strap being inserted into the insertion opening of the single quick adjustment mechanism and the protruding end of the single elongated tongue being inserted into the insertion opening of the single ratcheting assembly, so that the single closed loop is adapted to be looped about a limb of a patient,
    wherein the colored rigid insertion end is quickly pulled from the exit opening of the single quick adjustment mechanism until the single loop of the closed loop is snuggly wrapped about the limb, and the ratchet assembly is adjusted to further selectively ratchet and close the closed loop in order to tighten the closed loop more stringently about the limb effecting a tourniquet condition for the limb,
    wherein the single ratcheting assembly includes:
        a ratcheting frame with the insertion opening and the exiting opening;
        a ratcheting lever having a lifting end and an opposite end with lever teeth, the opposite end being pivotally attached to the ratchet frame; and
        a pivotal locking block on the ratchet frame which in a locking position which locks against a portion of the teethed surface on the elongated tongue and prevents the single elongated tongue from separating from the ratcheting assembly, the pivotal locking block having a release position which allows for elongated tongue to be separated from the ratcheting assembly, and wherein the single quick adjustment mechanism includes:
a cam lock anchor having the insertion opening and the exit opening; and
a cam lock lever having a lift end and an opposite end that is pivotally attached to the cam lock anchor, wherein lifting of the lift end of the lever provides for instant loosening of the colored end of the single belt strap from the single quick adjustment mechanism.

2. A method of quickly using a single loop tourniquet, consisting of the steps of:
providing a single belt strap having a colored rigid insertion end and an opposite end having a single ratcheting assembly having an insertion opening and an exit opening;
providing a single elongated tongue having a protruding end with a teethed surface, the tongue extending from a single quick adjustment mechanism that has an insertion opening and an exit opening,
forming a single closed loop from the colored rigid insertion end of the single belt strap being inserted into the insertion opening of the single quick adjustment mechanism and the protruding end of the single elongated tongue being inserted into the insertion opening of the single ratcheting assembly;
looping the single closed loop to be adapted about a limb of a patient,
quickly pulling the colored rigid insertion end from the exit opening of the single quick adjustment mechanism until the single loop of the closed loop is snuggly wrapped about the limb,
adjusting the ratchet assembly to further selectively ratchet and close the closed loop in order to tighten the closed loop more stringently about the limb effecting a tourniquet condition for the limb,
providing the single ratcheting assembly to include:
a ratcheting frame with the insertion opening and the exiting opening;
a ratcheting lever having a lifting end and an opposite end with lever teeth, the opposite end being pivotally attached to the ratchet frame; and
a pivotal locking block on the ratchet frame which in a locking position which locks against a portion of the teethed surface on the elongated tongue and prevents the single elongated tongue from separating from the ratcheting assembly, the pivotal locking block having a release position which allows for elongated tongue to be separated from the ratcheting assembly, and
providing the single quick adjustment mechanism to include:
a cam lock anchor having the insertion opening and the exit opening; and
a cam lock lever having a lift end and an opposite end that is pivotally attached to the cam lock anchor, wherein lifting of the lift end of the lever provides for instant loosening of the colored end of the single belt strap from the single quick adjustment mechanism.

\* \* \* \* \*